(12) United States Patent  (10) Patent No.: US 8,894,695 B2
Moore et al.  (45) Date of Patent: *Nov. 25, 2014

(54) OCCIPITAL PLATE FOR CERVICAL FIXATION

(75) Inventors: Jennifer Moore, Summit Point, WV (US); John Kostuik, Phoenix, AZ (US); Steve A. Brown, Timonium, MD (US)

(73) Assignee: K2M, Inc., Leesburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/539,541

(22) Filed: Jul. 2, 2012

(65) Prior Publication Data

US 2012/0271360 A1  Oct. 25, 2012

Related U.S. Application Data (63) Continuation of application No. 12/578,274, filed on Oct. 13, 2009, now Pat. No. 8,226,695.

(60) Provisional application No. 61/195,825, filed on Oct. 10, 2008.

(51) Int. Cl.
A61B 17/80 (2006.01)
A61B 17/70 (2006.01)

(52) U.S. Cl.
CPC ......... A61B 17/7044 (2013.01); A61B 17/7055 (2013.01)
USPC .................................................. 606/286

(58) Field of Classification Search
USPC ......... 606/246, 250, 251, 264, 265, 267, 270, 606/280, 281, 283, 284, 286
See application file for complete search history.

(56) References Cited

U.S. PATENT DOCUMENTS

| | | |
|---|---|---|
| 4,905,679 A | 3/1990 | Morgan |
| 4,923,471 A | 5/1990 | Morgan |
| 5,324,290 A | 6/1994 | Zdeblick et al. |
| 5,681,312 A | 10/1997 | Yuan et al. |
| 5,702,392 A | 12/1997 | Wu et al. |
| 6,010,503 A * | 1/2000 | Richelsoph et al. ......... 606/278 |
| 6,113,599 A | 9/2000 | Landsberger |
| 6,254,603 B1 | 7/2001 | Gertzbein et al. |
| 6,524,315 B1 | 2/2003 | Selvitelli et al. |
| 6,547,790 B2 | 4/2003 | Harkey, III et al. |
| 7,087,057 B2 * | 8/2006 | Konieczynski et al. ...... 606/278 |
| 7,232,441 B2 | 6/2007 | Altarac et al. |
| 7,303,563 B2 | 12/2007 | Poyner et al. |
| 7,445,627 B2 * | 11/2008 | Hawkes et al. ............... 606/269 |
| 7,618,443 B2 * | 11/2009 | Abdou .......................... 606/278 |
| 2005/0124994 A1 | 6/2005 | Berger et al. |
| 2005/0240185 A1 | 10/2005 | Boomer et al. |
| 2006/0155284 A1 | 7/2006 | Doherty et al. |
| 2006/0229610 A1 | 10/2006 | Piehl |
| 2007/0233119 A1 | 10/2007 | Markworth |
| 2007/0233138 A1 * | 10/2007 | Figueroa et al. ............... 606/87 |
| 2007/0299441 A1 | 12/2007 | Hoffman et al. |
| 2008/0086124 A1 | 4/2008 | Forton et al. |
| 2008/0177313 A1 | 7/2008 | Lemoine et al. |

* cited by examiner

*Primary Examiner* — Anu Ramana
(74) *Attorney, Agent, or Firm* — Carter, DeLuca, Farrell & Schmidt, LLP (57) ABSTRACT

An adjustable occipital plate includes a central body portion having a plurality of arms extending therefrom in a generally Y-shaped configuration. Two of the arms include elongate slots for slidably receiving retaining members therein. Each retaining member includes a U-shaped channel for receiving a spine rod and a set screw. The central body portion and one arm include openings for receiving bone screws therein. Each of the arms may be angled with respect to the central body portion.

9 Claims, 8 Drawing Sheets

FIG. 9

OCCIPITAL PLATE FOR CERVICAL FIXATION

CROSS-REFERENCE TO RELATED APPLICATIONS

This application is a continuation application of U.S. patent application Ser. No. 12/578,274, filed on Oct. 13, 2009, which claims priority to, and the benefit of, U.S. Provisional Patent Application No. 61/195,825, filed Oct. 10, 2008. The entire contents of each of these prior applications are hereby incorporated by reference.

BACKGROUND

1. Technical Field

The present disclosure relates to devices for bone fixation. More particularly, the present disclosure relates to an occipital plate for cervical fixation.

2. Background of Related Art

The occipitocervical junction, which comprises the occiput, atlas, and axis, represents a unique and complex interface between the cranium and the rostral cervical spine. More than 50% of the rotation and flexion-extension of the head and neck occurs in that region. In addition, the osseous articulations and their ligamentous support structures must resist force in eight axes of rotation. These include flexion, extension, bilateral lateral bending; and bilateral rotation, distraction, and axial loading. Instrumentation constructs not only must resist forces in all of these vectors, but also must resist the significant lever arm created by the suboccipital bone and the cervical spine, which meet at a 50° angle. Any instrumentation construct designed for use in this region must, therefore, have adequate dimensions to interface with the osseous structures of the spinal structures as well as have sufficient rigidity and purchase to resist these forces until bone fusion can occur. Great flexibility must be afforded to allow for the multiple anatomical variations seen in this region.

In the early 1900s occipitocervical instability and lesions located at the occipitocervical junction were considered inoperable and terminal. Since the first description of an occipitocervical fusion by Forrester in 1927, multiple methods of fusion in this region have been described. Descriptions of simple onlay bone grafts with halo immobilization; wire, pin, or hook constructs; rigid metallic loops and rectangles fixed to the bone with either screws or wires; and most recently, plate or rod constructs with screws have all been described. In general, the evolution of this technology has focused on providing increasingly more rigid constructs to facilitate bone fusion and to minimize the need for and duration of external immobilization.

A common technique for fixing occipitocervical instability is the use of an inverted Y-shaped screw plate. Using this technique, the plate is secured to C1-2 with transarticular screws and to the suboccipital bone with paramedian screws. The suboccipital bone varies in thickness, with a mean thickness of about 14 mm. Screws must be carefully selected to provide adequate purchase, yet avoid cerebellar injury. Utilizing the maximum screw length possible is critical, because shorter screws do have reduced resistance to pullout. If stabilization is required below the C1-2 level, then lateral mass screws can be placed through additional holes in a longer plate to include these levels as well. A bone graft is again added to promote fusion. The Y-shaped plate, in combination with transarticular screws, is an economically favorable alternative. Immediate postoperative stabilization is achieved and very low rates of pseudoarthrosis have been reported.

SUMMARY

The present disclosure relates to an adjustable occipital plate having a central body portion and a plurality of arms extending therefrom in a generally Y-shaped configuration. The central body portion and at least one of the arms include an opening for threadably receiving a bone screw. Each arm may be joined to the central body portion by a bendable joint that allows each arm to be individually angled with respect to the central body portion.

Further, at least one of the arms includes an elongate slot for slidably receiving a retaining member or screw housing. The screw housing includes a shank having threads formed thereon and a head. The head includes a pair of opposed upstanding walls defining a U-shaped channel therebetween that is configured and adapted for receiving a portion of a spine rod. The upstanding walls include threads for threadably engaging threads of a set screw. Once the spine rod is positioned relative to the occipital plate and a portion of the spine rod is disposed in the U-shaped channel, the set screw is threaded into the screw housing, thereby securing the spine rod to the occipital plate. The at least one arm including the elongate slot further includes a channel disposed on one side. The channel is configured and dimensioned for slidably receiving a nut therein. The nut is threadably engaged with the threads on the shank of the screw housing, thereby retaining the screw housing to the respective arm of the occipital plate. The screw housing may be welded to the nut and may also be rotatable in the elongate slot since the nut may be rotatable within the channel.

A plurality of bone screws is insertable through the openings of the occipital plate. In one embodiment, the screws are formed from a harder material than the occipital plate. As such, when the bone screws are threaded into the openings, a lip of each opening deforms such that the bone screw is affixed to the occipital plate and resists backing out from the occipital plate.

BRIEF DESCRIPTION OF THE DRAWINGS

Embodiments of the presently disclosed occipital plate are described herein with reference to the accompanying drawings, wherein.

DETAILED DESCRIPTION

Various embodiments of the presently disclosed occipital plate for cervical fixation will now be described in detail with reference to the drawings, wherein like reference numerals identify similar or identical elements. In the drawings and in the description that follows, the term "proximal," will refer to the end of a device or system that is closest to the operator, while the term "distal" will refer to the end of the device or system that is farthest from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e. away from the middle of the body of the patient). The term "posterior" indicates a direction toward the patient's back, and the term "anterior" indicates a direction toward the patient's front. Additionally, in the drawings and in the description that follows, terms such as front, rear, upper, lower, top, bottom, and the similar directional terms are used simply for convenience of description and are not intended to limit the disclosure attached hereto.

Figure 1:
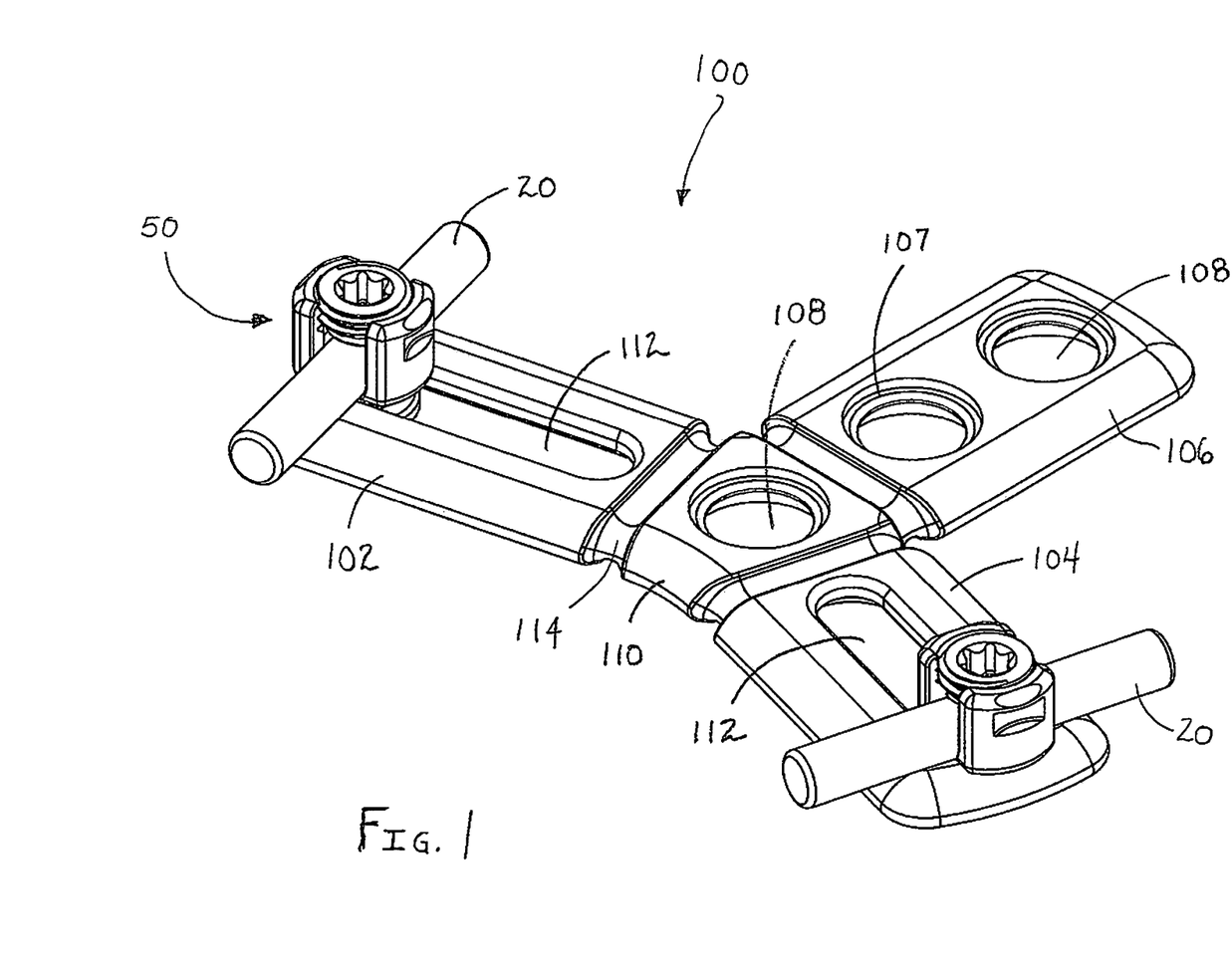
FIG. 1 is a top elevational view of the presently disclosed occipital plate with rods coupled to retaining members.
Figure 3:
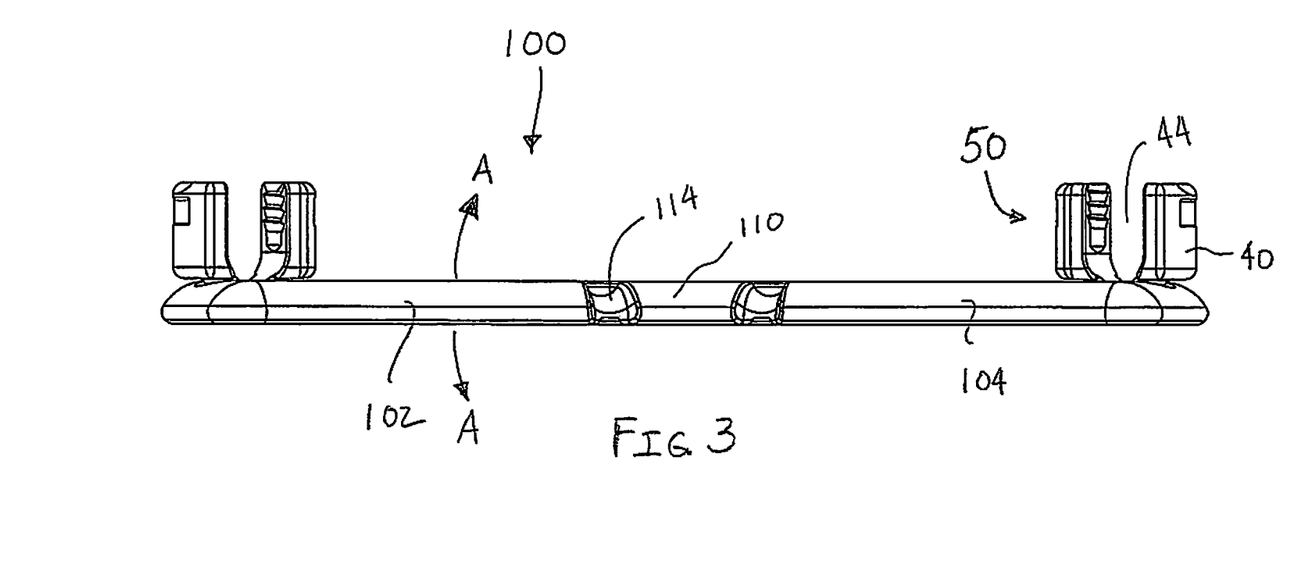
FIG. 3 is an end view of the occipital plate of FIG. 1 with the rods removed.

Referring initially to FIG. 1, an occipital plate or adjustable occipital plate 100 is illustrated. The adjustable occipital plate 100 includes a central portion 110 having an opening 108 therethrough. The opening 108 is generally circular and includes a generally circular lip 107. In addition, the adjustable occipital plate 100 includes a first arm 102 and a second arm 104 extending from the central body portion 110 at an angle thereto. A third arm 106 also extends from the central body portion 110 such that the first arm 102, the second arm 104, and the third arm 106 define a generally Y-shaped configuration of the adjustable occipital plate 100. In one embodiment, the adjustable occipital plate 100 is formed from commercially pure titanium. A deformable joint 114 is located between the central portion 110 and each of the arms 102, 104, and 106. The joint 114 may be formed such that each of the arms 102, 104, and 106 are bendable with respect to the central portion as shown by directional arrows A in FIG. 3. Thus, the arms 102, 104, and 106 may be bent relative to the central portion 110 and define acute angles with respect thereto. Each arm 102, 104, and 106 may be individually bent without regard to the remaining arms.

Figure 2A:
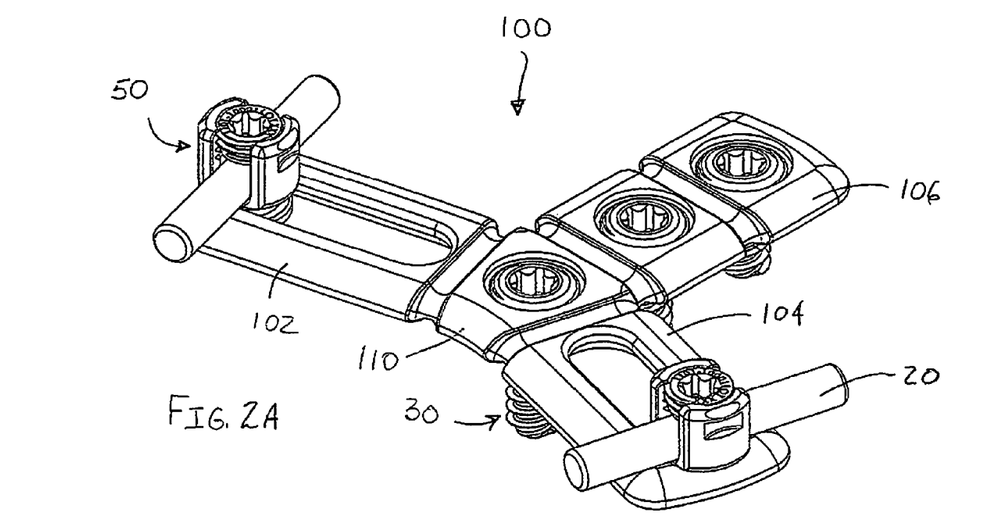
FIG. 2A is a top elevational view of the occipital plate of FIG. 1 with bone fasteners disposed in openings of the occipital plate.
Figure 2B:
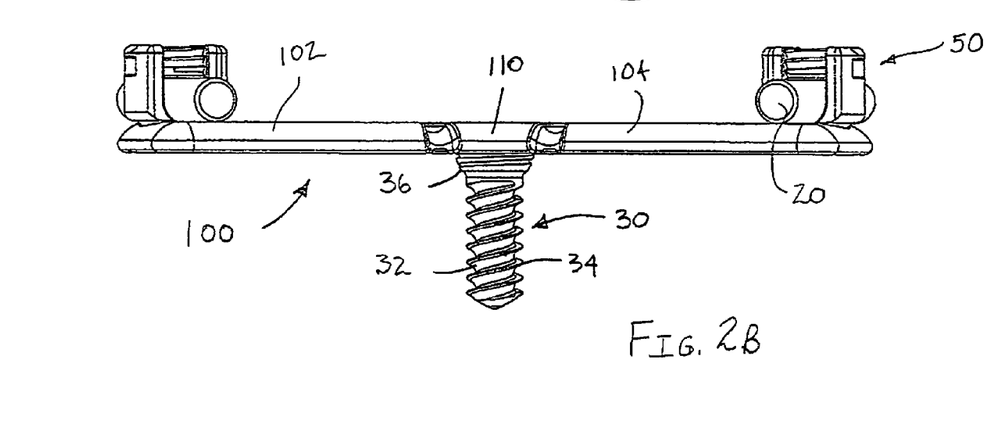
FIG. 2B is a side view of the occipital plate of FIG. 2A.

With additional reference to FIGS. 2A and 2B, each of the first and second arms 102, 104 includes an elongate oval slot 112, while the third arm includes openings 108. Each of the openings 108 is configured for receiving a bone screw 30 therein. Bone screw 30 includes a shank 32 extending from a head. The head of the bone screw 30 preferably includes threads 36 having a first pitch and the shank 32 includes threads 34 having a second pitch that may be different from the first pitch of threads 36. In one embodiment, the bone screw 30 is formed from a titanium alloy (e.g. Ti-6A1-4V) or another material that is harder than the material used to form the occipital plate 100. In this configuration, when the bone screw 30 is installed in the opening 108, the threads 36 of the head of the bone screw engage the lip 107 of the opening. Since the bone screw 30 is formed from harder material than that of the lip 107, the lip 107 deforms, thereby securing the bone screw 30 and plate 100 to each other. In this arrangement, the bone screw 30 resists backing out of the opening 108. This type of screw locking arrangement is disclosed and shown in U.S. Pat. No. 6,322,562 to Wolter, the entire contents of which are hereby incorporated by reference herein.

The oval slots 112 are configured for receiving a screw housing 50 therein. In this configuration, the screw housings 50 are repositionable throughout a plurality of positions along a length of the oval slots 112. A spinal rod 20 is coupled to each of the screw housings 50.

Figure 4A:
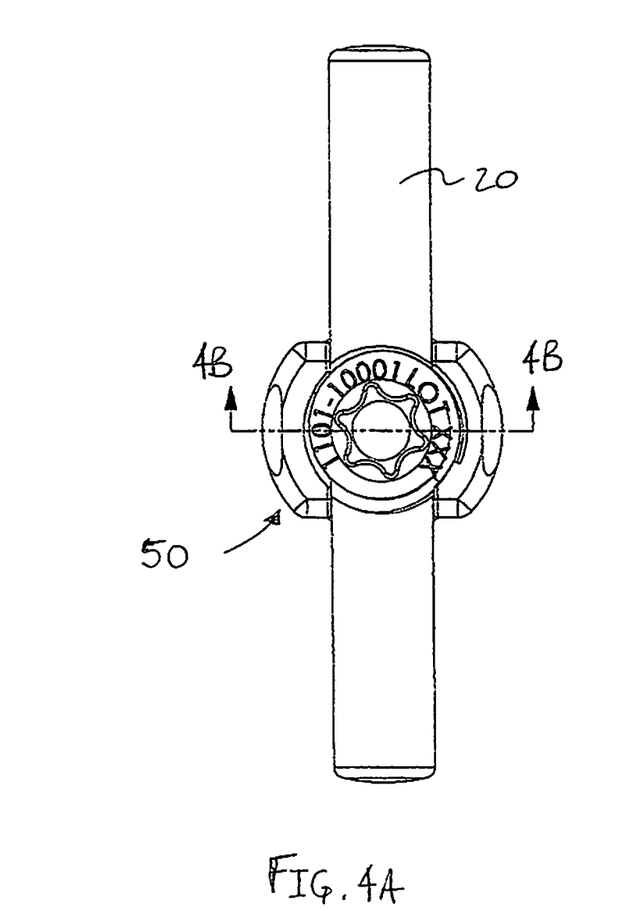
FIG. 4A is a top view of a rod coupled to a retaining member.
Figure 4B:
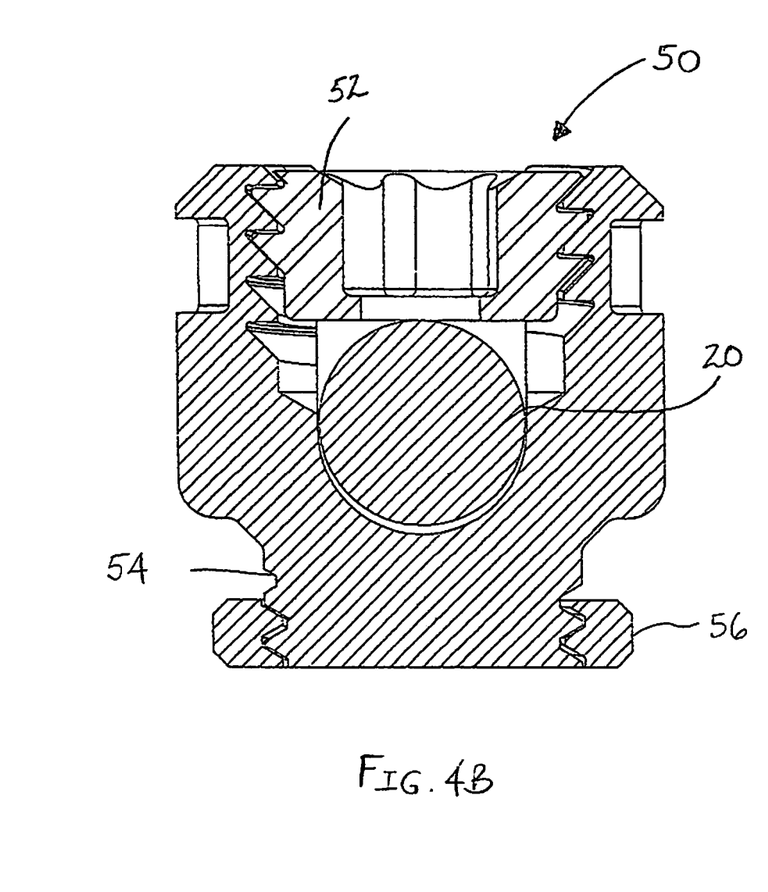
FIG. 4B is a side cross-sectional view of the rod and retaining member of FIG. 4A taken along section line 4B-4B.
Figure 5:
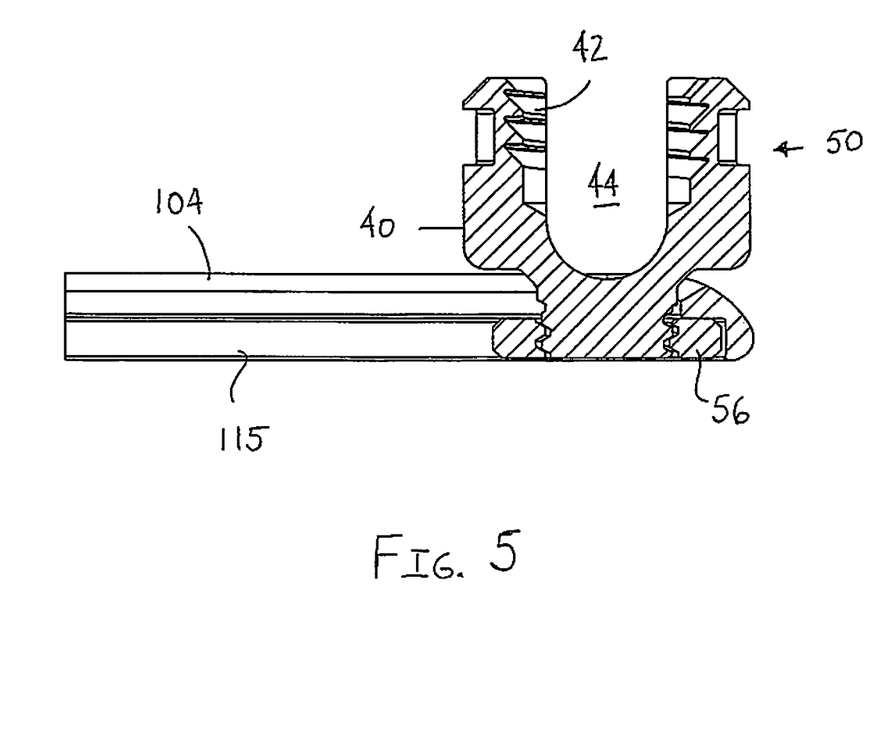
FIG. 5 is a side, part cross-sectional view of an arm and the retaining member of the occipital plate of FIG. 2B.
Figure 6:
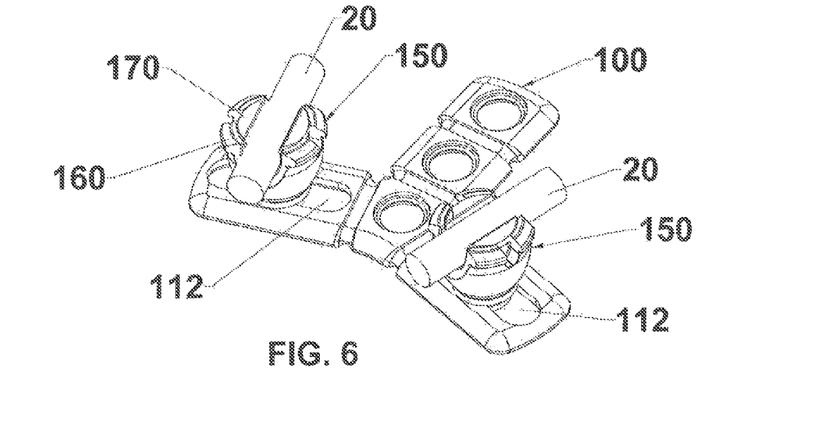
FIG. 6 is a top elevation view of another embodiment of the presently disclosed occipital plate with rods coupled to retaining members.

Referring additionally to FIGS. 4A, 4B, and 5, each screw housing 50 includes a head 40 having upstanding walls with internal threads 42 that define a U-shaped channel 44 therebetween. The U-shaped channel 44 is configured for receiving the spinal rod 20 therein. The internal threads 42 of the head 40 are configured for engaging external threads of a set screw 52. Each screw housing 50 is secured to its respective oval slot 112 by a nut 56.

Further still, the screw housing 50 includes a shank 54 having threads thereon for engaging the threading of the nut 56. Once assembled, the shank 54 is welded to the nut 56. Since the nut 56 is round, it is able to rotate in a channel 115 that is located on the underside of the oval slot 112, thereby allowing the screw housing 50 to rotate relative to its respective arm 102, 104. As such, the screw housing 50 is easily repositionable and rotatable for accommodating the spinal rod 20. The channel 115 allows the nut 56 and the screw housing 50 to slide along the length of the oval slot 112 without the nut 56 separating from the channel 115. Once the screw housing 50 is in its desired position, the physician installs the spinal rod 20 in the U-shaped channel 44 of the screw housing 50. After the spinal rod 20 is positioned in the U-shaped channel 44, the physician threads the set screw 52 into the head 50 and tightens the set screw 52 which causes the nut 56 and rod 20 to be tightened against an upper surface of the respective arm 102, 104 to hold the spinal rod 20 in position. Finally, the physician installs one or more other bone screws 30 into the openings 108 and secures the adjustable occipital plate 100. Thus, the spinal rod 20 and screw housing 50 construct is secured to the occiput region of the patient's cranium.

Referring to FIGS. 6-9, the oval slots 112 of the occipital plate 100 receives a housing 150 in accordance with the present disclosure. The housing 150 includes a shank 154, a pin 130, an outer housing or coupling 160, and an inner housing or collet 170.

The coupling 160 includes an annular body portion 162 having an opening 164 extending axially therethrough. Additionally, the coupling 160 includes a plurality of fingers 166 that are located in opposing regions of the coupling 160 and define a saddle 168 having a generally U-shaped configuration. The U-shaped saddle 168 is configured and dimensioned for receiving one of the rods 20.

Figure 7:
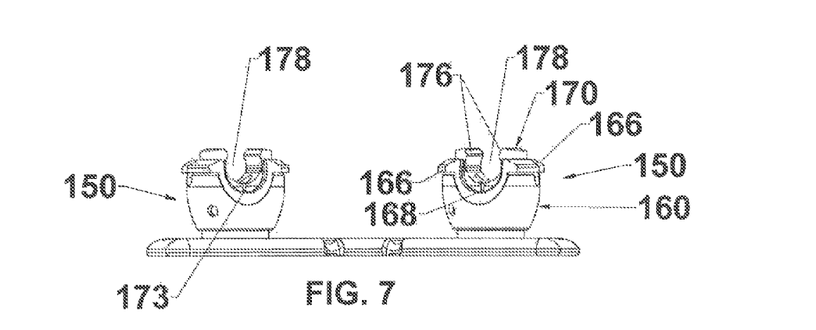
FIG. 7 is an end view of the occipital plate of FIG. 6 with the rods removed.
Figure 8A:
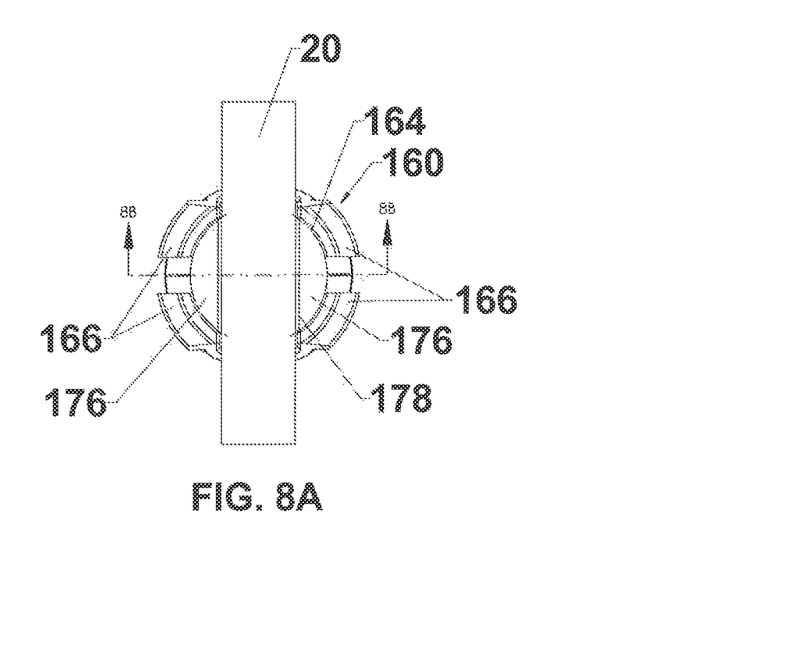
FIG. 8A is a top view of a rod coupled to a retaining member.
Figure 8B:
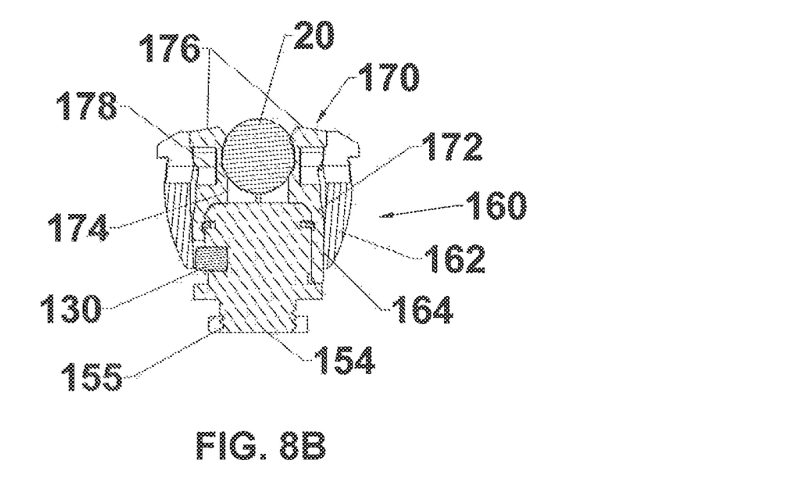
FIG. 8B is a side cross-sectional view of the rod and retaining member of FIG. 8A taken along section line 8B-8B.
Figure 9:
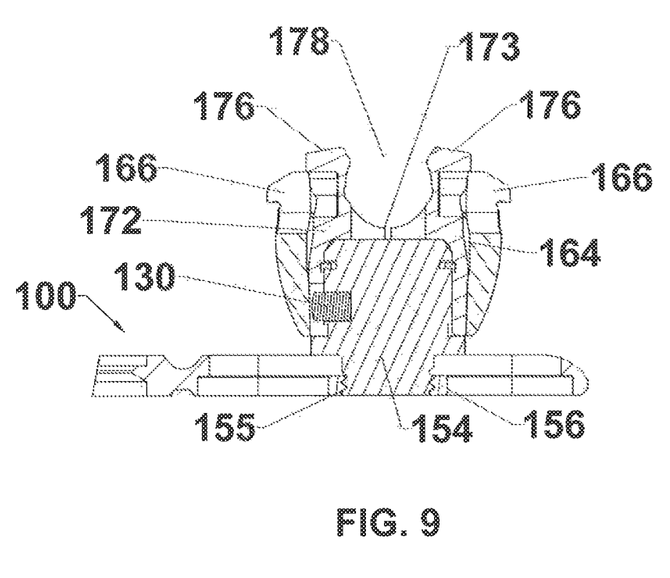
FIG. 9 is a side, part cross-sectional view of an arm and the retaining member of the occipital plate of FIG. 7.

With continued reference to FIGS. 7-9, the collet 170 has a generally cylindrical body portion 172 with an opening 174 extending axially therethrough. A pair of upstanding wings 176 defines a channel or saddle 178 having a generally U-shaped configuration. The saddle 178 is configured and dimensioned for receiving the rod 20. The body portion 172 includes a slot 173 that extends from the nadir of the saddle 178 towards the bottom of the body portion 172 and essentially bisects the body portion 172 along a central axis, and defines two sections of the body portion. Preferably, the slot 173 does not extend all the way through the body portion 172. Although less desirable, such a full slot could be used. This arrangement permits each of the wings 176 to flex towards and away from each other. The dimensions of the saddle 178 vary according to the flexure of the wings 176. As the wings 176 are moved closer to each other, the saddle 178 decreases in size and when the wings 176 are moved away from each other, the saddle 178 increases in size. Allowing the saddle 178 to vary in size permits the collet 170 to accommodate rods 20 having differing outside diameters. Alternatively, compressing the wings 176 towards each other increasingly engages the outer surface of the rod 20 located in the saddle 178, thereby frictionally securing the rod 20 in a desired position.

The shank 154 includes a helical thread 155 formed thereon for engaging the threading of the nut 156 as detailed above.

The housing 150 will now be discussed as assembled for use. The collet 170 is seated atop the shank 154. The opening at the bottom of collet 170 is dimensioned and configured for receiving the shank 154. As such, the collet 170 and the shank 154 are rotatable in relation to each other, thereby allowing the shank 154 to be repositioned in a plurality of orientations relative to the collet 170. The combination of the collet 170 and shank 154 is inserted into the coupling 160. The pin 130 aligns the collet 170 and the coupling 160 for maintaining a fixed relationship therebetween.

Each of the embodiments described above are provided for illustrative purposes only. It will be understood that various modifications may be made to the embodiments of the presently disclosed vertebral body staple. By way of example only, it is contemplated that the rod receiving portion of the housing may include a taper lock for locking the rod relative to the housing, rather than a set screw design as shown, A suitable taper lock configuration may be adapted from the taper lock design shown in International Patent Application Number PCT/US/2008/080682 filed on Oct. 22, 2008 and published as international application WO 2009/055407, the entire contents of which are incorporated herein by reference. Therefore, the above description should not be construed as limiting, but merely as exemplifications of embodiments. Those skilled in the art will envision other modifications within the scope and spirit of the present disclosure.

What is claimed is:

1. A bone fastening assembly comprising:
   a plate having a central portion with an opening;
   a first arm extending from the central portion, the first arm including at least one orifice;
   a second arm and a third arm, the second and third arms extending from the central portion, each of the second and third arms defining an elongated slot, each of the second and third arms having a top surface and a bottom surface; and
   a retaining member disposed in each of the elongated slots, each retaining member including a housing having a shank extending therefrom and a nut, the housing positioned on one side of the second and third arms respectively, the nut threadably coupled to the shank such that the retaining member is repositionable along a length of the elongated slot and retained therein, the nut positioned between the top surface and the bottom surface, the housing including a channel for retaining a portion of a rod.

2. The bone fastening assembly of claim 1, wherein the retaining member is securable in one of a plurality of positions along the length of the elongated slot.

3. The bone fastening assembly of claim 1, wherein the rod-receiving channel defines a generally U-shaped configuration.

4. The bone fastening assembly of claim 1, wherein the housing defines threads adjacent the rod-receiving channel for receiving a set screw.

5. The bone fastening assembly of claim 1, wherein the at least one orifice is configured to receive a bone screw.

6. The bone fastening assembly of claim 1, wherein the opening is configured to receive a bone screw.

7. The bone fastening assembly of claim 1, wherein the first, second, and third arms are arranged to define a generally Y-shaped configuration.

8. The bone fastening assembly of claim 1, wherein a junction between the central portion of the plate and at least one of first, second, or third arms is deformable such that the at least one of first, second, or third arms is repositionable with respect to the central portion.

9. The bone fastening assembly of claim 1, wherein the housing includes an outer housing and an inner housing, the inner housing defining the channel, the outer and inner housings moveable relative to one another for securing a rod within the channel.

* * * * *